US007016456B2

(12) United States Patent
Basu et al.

(10) Patent No.: US 7,016,456 B2
(45) Date of Patent: Mar. 21, 2006

(54) METHOD AND APPARATUS FOR CALIBRATING VOLUMETRIC COMPUTED TOMOGRAPHY SYSTEMS

(75) Inventors: Samit Kumar Basu, Niskayuna, NY (US); Peter Michael Edic, Albany, NY (US); Bruno Kristiaan Bernard De Man, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 50 days.

(21) Appl. No.: 10/699,087

(22) Filed: Oct. 31, 2003

(65) Prior Publication Data

US 2005/0094771 A1   May 5, 2005

(51) Int. Cl.
*A61B 6/03* (2006.01)
(52) U.S. Cl. .................... 378/18; 378/205; 378/207
(58) Field of Classification Search .................. 378/4, 378/18, 205, 207; 250/505.1
See application file for complete search history.

(56) References Cited

U.S. PATENT DOCUMENTS

| | | | |
|---|---|---|---|
| 4,296,329 A | 10/1981 | Mirabella | |
| 5,056,130 A | 10/1991 | Engel | |
| 5,442,674 A * | 8/1995 | Picard et al. | 378/207 |
| 6,000,847 A * | 12/1999 | Close et al. | 378/207 |
| 6,419,680 B1 | 7/2002 | Cosman et al. | |
| 6,471,400 B1 | 10/2002 | Simanovsky et al. | |
| 6,491,430 B1 | 12/2002 | Seissler | |
| 6,632,020 B1 | 10/2003 | Kaufhold et al. | |
| 6,715,918 B1 * | 4/2004 | Mitschke et al. | 378/207 |

* cited by examiner

*Primary Examiner*—Edward J. Glick
*Assistant Examiner*—Chih-Cheng Glen Kao
(74) *Attorney, Agent, or Firm*—Fletcher Yoder (57) ABSTRACT

The present invention provides a method for determining a geometry of a scanning volumetric computed tomographic (CT) system having a rotation axis, a rotational plane, an x-ray source and a detector. The method includes scanning a phantom having a series of spatially separated discrete markers with the scanning volumetric computed tomographic system, wherein the markers are configured on a supporting structure of the phantom so as to permit separate identification of each marker in a collection of projection images. The method further includes locating images of the markers in each projection, using the located marker images to assign marker locations to tracks, and using the assigned tracks, determining a relative alignment between the detector, the source, and the rotation axis of the scanning volumetric computed tomographic system.

18 Claims, 6 Drawing Sheets

METHOD AND APPARATUS FOR CALIBRATING VOLUMETRIC COMPUTED TOMOGRAPHY SYSTEMS

STATEMENT REGARDING FEDERALLY SPONSORED RESEARCH & DEVELOPMENT

The U.S. Government has a paid-up license in this invention and the right in limited circumstances to require the patent owner to license others on reasonable terms as provided by the terms of contract no. DAMD 170220004 awarded by the Department of Defense.

BACKGROUND OF THE INVENTION

This invention relates generally to computed tomographic systems and more particularly to methods and apparatus for determining geometric parameters from volumetric computed tomography (CT) systems.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object impinges upon an array of radiation detectors. The intensity of the attenuated beam radiation received at the detector array is dependent upon the attenuation of the x-ray beam by the object. Each detector element of the array produces a separate electrical signal that is a measurement of the beam intensity at the detector location. The x-ray intensity measurements from all the detectors are acquired separately to produce a transmission profile.

In known third generation CT systems the x-ray source and the detector array are rotated with a gantry within the imaging plane and around the object to be imaged so that the angle at which the x-ray beam intersects the object constantly changes. A group of processed x-ray intensity measurements that correspond to the line integrals of the continuous linear attenuation coefficient within the object being imaged, i.e., projection data, from the detector array at one gantry angle is referred to as a "view." A "scan" of the object comprises a set of views made at different gantry angles, or view angles, during one revolution the x-ray source and detector about the object being imaged. In an axial scan, the projection data is processed to construct an image that corresponds to linear attenuation coefficient within a two-dimensional slice taken through the object. One method of reconstructing an image from a set of projection data is referred to in the art as the filtered back-projection technique. This process converts the projection data measurements from a scan into integers called "CT numbers" or "Hounsfield units" which are used to control the brightness of a corresponding pixel in a cathode ray tube display.

At least one known detector within a CT imaging system includes a plurality of detector modules, each having a scintillator array optically coupled to a semiconductor photodiode array that detects light output by the scintillator array. These known detector module assemblies require an increasing number of scintillator/diode rows along the longitudinal or Z direction in the object, together with associated electronics, to support a desire for increasing the axial coverage of the x-ray beam on the object per CT rotation. The increase in axial coverage on the object allows reconstruction of more CT slices per gantry rotation.

With the introduction of multi-row and volumetric CT scanners, including gantry-based and benchtop-type scanners, it has become necessary to determine critical alignment parameters beyond those necessary for traditional two-dimensional scanners. Without these critical alignment parameters, it is difficult or impossible to obtain adequate image quality from a scanner, as the image reconstruction process requires an accurate knowledge of scanner geometry to avoid artifacts and blurring in reconstructed images. Furthermore, in some volumetric CT (VCT) systems, it is necessary to physically adjust the orientations of the various components to properly alignment the imaging system.

For single slice CT scanner, it is known that all relevant parameters for alignment can be determined from a single scan of one or two point-like objects or pins. "Pin scans" can be used to extract the magnification of a CT system as well as the center of rotation in a straightforward manner. This technique is not applicable to VCT scanners, for which a number of additional parameters are required.

At least one known technique for aligning VCT scanners uses a phantom of special construction. This phantom uses a series of small physical balls (e.g., "BBs") that are located on a helix at a surface of a cylinder. The projection image of this phantom can be used to extract the exact system geometry at each view position, thus providing the required geometrical information for image reconstruction or system alignment, if the phantom uses a sufficient number of BBs. However, such phantoms work only over a limited range of geometries. In particular, the diameter of the cylinder and pitch of the helical matrix of the phantom limit the utility of such phantoms to a narrow range of magnifications and cone angles. Also, calibration methods using such phantoms are poorly conditioned, and it is difficult to use the resulting geometry information to reliably adjust the physical characteristics of the scanner.

BRIEF DESCRIPTION OF THE INVENTION

Some configurations of the present invention therefore provide a phantom for a volumetric computed tomography system. The phantom includes an essentially transparent or partially transparent supporting structure, and a plurality of discrete, essentially opaque markers spaced apart from one another on or in the supporting structure. The plurality of markers are configured (for example, by their spacing) so as not to overlap when scanned over a range of view angles by a volumetric computed tomography system. Also, the markers are configured on the supporting structure so as to permit separate identification of each said marker within a collection of projection images (for example, by one marker having a larger size than the others).

In some configurations, the present invention provides a method for determining a geometry of a scanning volumetric computed tomographic (CT) system having a rotation axis, a rotational plane, an x-ray source and a detector. The method includes scanning a phantom having a series of spatially separated discrete markers with the scanning volumetric computed tomographic system, wherein the markers are configured on a supporting structure of the phantom so as to permit separate identification of each marker in a collection of projection images. The method further includes locating images of the markers in each projection image, using the located marker images to assign marker locations to tracks, and using the assigned tracks, determining a relative alignment between the detector, the x-ray source, and the rotation axis of the scanning volumetric computed tomographic system.

Also, some configurations of the present invention provide a method for determining geometry of a scanning volumetric computed tomographic (CT) system, in which the system has a rotation axis, a rotation plane, a radiation source other than an x-ray source, and a detector. The method includes scanning a phantom having a series of spatially separated discrete markers utilizing the radiation source other than an x-ray source, wherein the markers are configured on a supporting structure of the phantom so as to permit separate identification of each said marker in a collection of projection images. The method further includes locating images of the markers in each projection image, using the located marker images to assign marker locations to tracks; and using the assigned tracks, determining a relative alignment between the detector, the radiation source, and the rotation axis of the scanning volumetric computed tomographic system.

It will thus be appreciated that configurations of the present invention allow for a relatively simple determination of various geometric parameters of a volumetric computed tomographic system that is resistant to measurement errors and phantom construction errors. Configurations of the present invention are also useful with a wide range of geometries and magnifications.

DETAILED DESCRIPTION OF THE INVENTION

Figure 1:
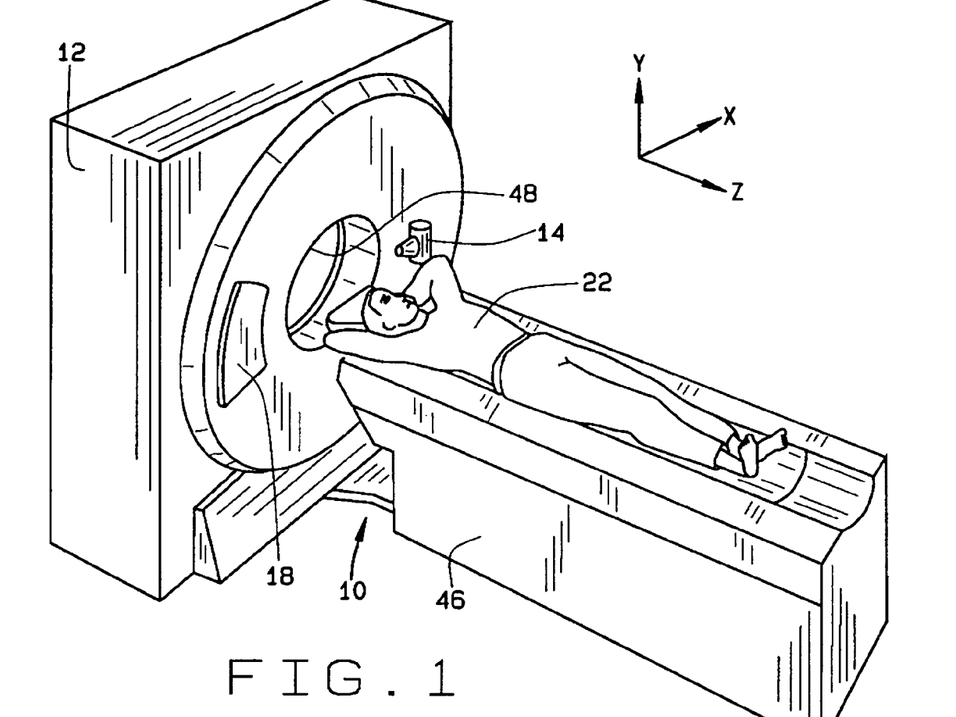
FIG. 1 is a pictorial diagram of a computed tomography imaging system.
Figure 2:
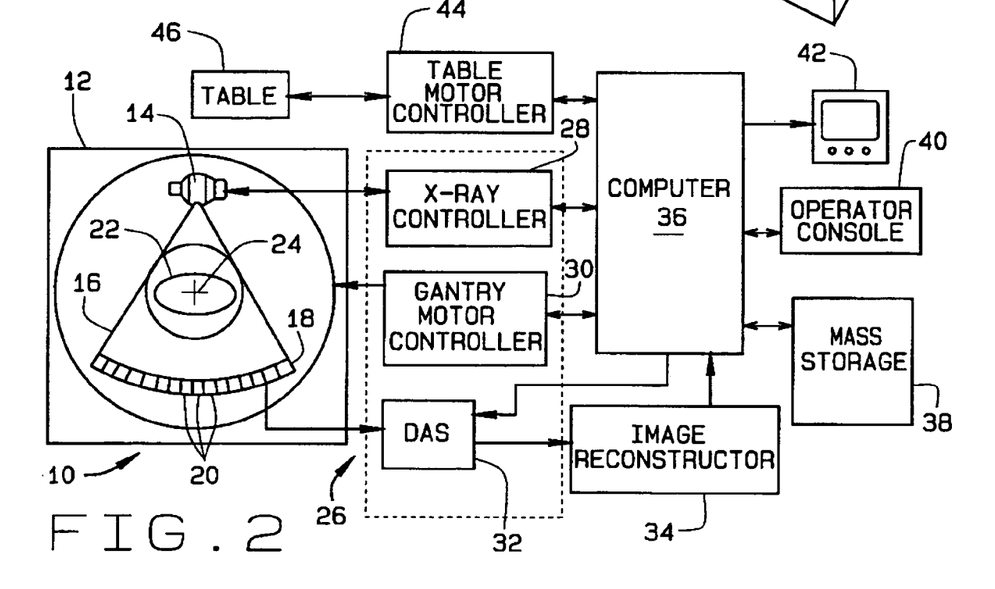
FIG. 2 is a block diagram of the computed tomography imaging system shown in FIG. 1.

Referring to FIG. 1 and FIG. 2, a computed tomography (CT) imaging system 10 is shown as including a gantry 12 representative of a third generation CT scanner. Gantry 12 has an x-ray source 14 that projects a beam of x-rays 16 toward a detector array 18 on opposite side of gantry 12. Detector array 18 is formed by detector elements 20 which together sense the projected x-rays that pass through an object 22, for example a medical patient. Each detector element 20 produces an electrical signal that represents the intensity of an impinging x-ray beam and allows computation of the attenuation of the beam as it passes through patient 22. During a scan to acquire x-ray projection data, a rotating portion of gantry 12 and the components mounted thereon rotate about a center of rotation 24. Detector array 18 may be fabricated in a single slice, multi-slice, or area configuration. In a multi-slice or area configuration, as in various configurations of the present invention, detector array 18 has a plurality of rows of detector elements 20, only one of which is shown in FIG. 2. In many configurations of the present invention, a multi-slice or area detector array is used to obtain volumetric images.

Rotation of a portion of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of a portion of gantry 12. A data acquisition system (DAS) 32 in control mechanism 26 samples analog data from detector elements 20 and converts the data to digital signals for subsequent processing. An image reconstructor 34 receives samples of the digitized x-ray data from DAS 32 and performs high speed image reconstruction. The reconstructed image is applied as an input to a computer 36 which stores the image in a storage device 38. In other embodiments, image reconstructor 34 is either hardware within computer 36 or software executed by computer 36.

Computer 36 also receives commands and scanning parameters from an operator via console 40 that has an input device such as a keyboard or a mouse. An associated cathode ray tube display 42 allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44 which controls a motorized table 46 to position patient 22 in gantry 12. Particularly, table 46 moves portions of patient 22 through gantry opening 48.

Figure 3:
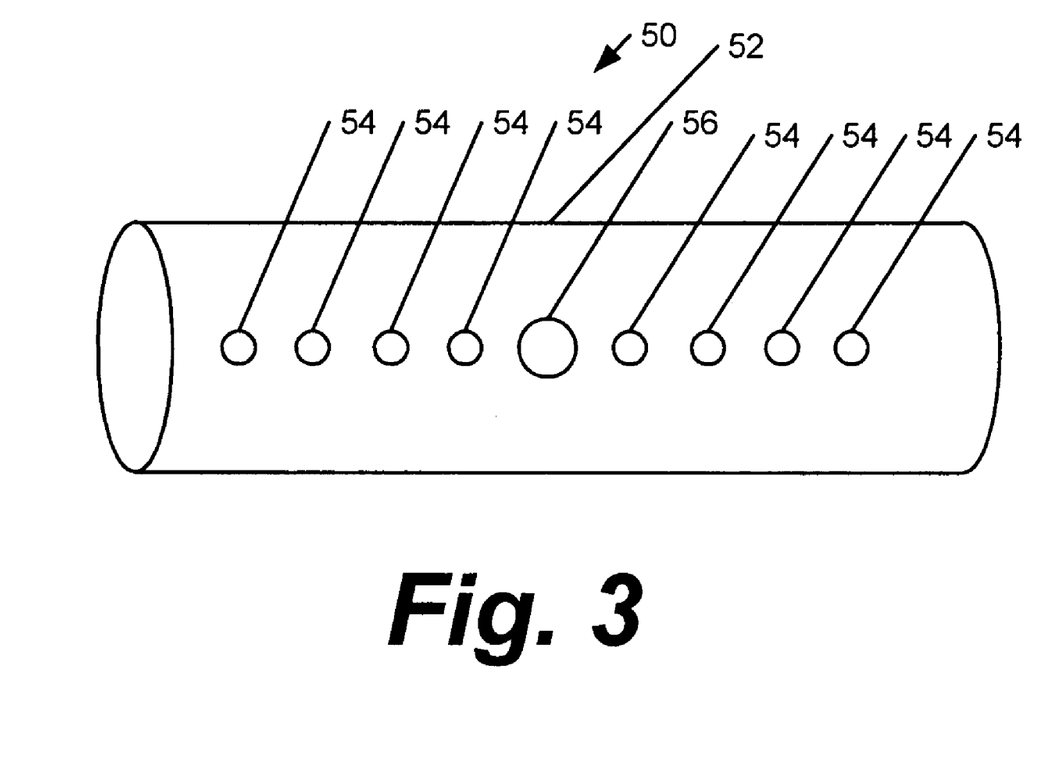
FIG. 3 is a longitudinal or side view of a configuration of a phantom of the present invention having a transparent or essentially transparent supporting structure and a linear configuration of markers.
Figure 4:
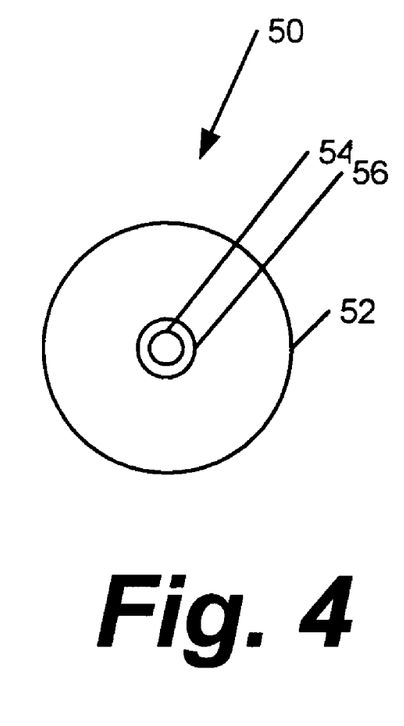
FIG. 4 is an end view of the phantom configuration of FIG. 3.

In some configurations of the present invention, critical geometric parameters of a volumetric CT imaging system 10 are obtained utilizing a scan of a calibration phantom 50. Referring to FIG. 3 and FIG. 4, various configurations of calibration phantom 50 comprise an essentially transparent or partially transparent supporting structure 52, for example, a plastic cylinder. By "transparent" or "partially transparent," it is meant that the structure is transparent or partially transparent to radiation produced by source 14 (for example, x-ray radiation, if source 14 is an x-ray source), not necessarily to visible light. Conversely, "opaque" and "essentially opaque" as used herein mean that the structure is opaque or essentially opaque to radiation produced by source 14 (for example, x-ray radiation, if source 14 is an x-ray source), not necessarily to visible light. A plurality of discrete, essentially opaque markers 54 and 56 are spaced apart from one another on or in supporting structure 52. Markers 54 and 56 are configured not to overlap one another over a range of view angles when scanned by volumetric CT imaging system 10. Such configuration is accomplished in various configurations by the spacing of markers 54 and 56 from one another. In addition, markers 54 and 56 are configured on the supporting structure so as to permit separate identification of each marker 54 and 56 within each projection image. In some configurations, such configuration is accomplished by making one marker 56 larger than all other markers 54. As a result, marker 56 can be readily identified in projection images. All other markers 54 are readily identified by their relative location with respect to marker 56 and/or with respect to each other.

Figure 5:
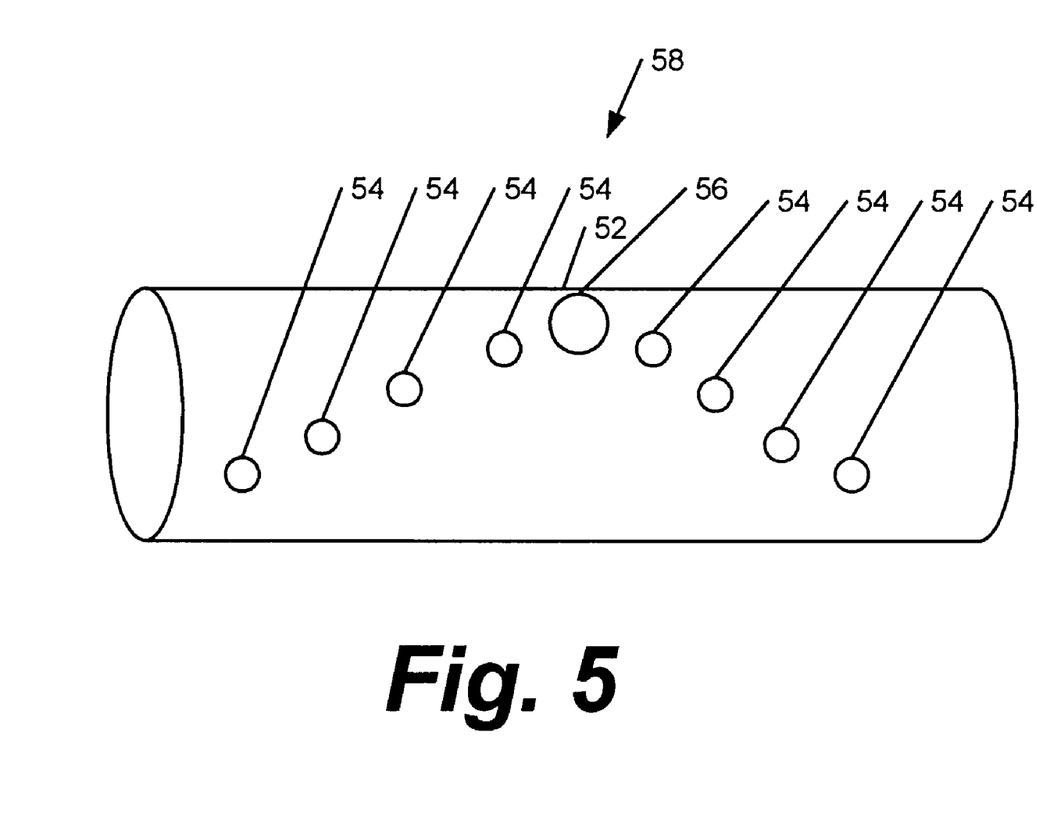
FIG. 5 is a longitudinal side view of a configuration of a phantom of the present invention having a transparent or essentially transparent supporting structure and a helical configuration of markers.
Figure 6:
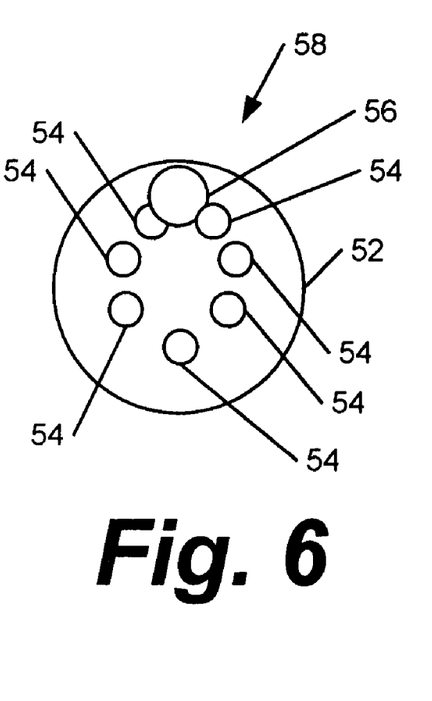
FIG. 6 is an end view of the phantom configuration of FIG. 5.

In many configurations, markers 54 and 56 comprise spaced apart spheres (or BBs), one of which (56) is larger than the others (54), and markers 54 and 56 comprise a metal or metal alloy. Markers 54 and 56 are arranged in a linear array on or in supporting structure 52 in configurations represented by FIG. 3 and FIG. 4. However, in some other configurations, such as those represented by phantom 58 in FIG. 5 and FIG. 6, markers 54 and 56 are arranged in another configuration, such as on a helical trajectory on or in supporting structure 52. Markers 54 and 56 may either be embedded in supporting structure 52 or affixed to a surface thereof.

In some configurations, supporting structure 52 comprises a solid plastic cylinder, and markers 54 and 56 are embedded in structure 52. However, the supporting structure of the phantom need not comprise plastic nor need it be solid. Thus, in some configurations and referring to FIG. 7 and FIG. 8, some other phantom configurations 60 comprise a wire frame supporting structure 62 on which markers 54 and 56 are supported. Wire frame supporting structure 62 is essentially transparent to x-rays, in that most of the structure is empty space and most x-ray radiation passing through the volume enclosed by structure 62 never encounters a wire.

Figures 7, 8:
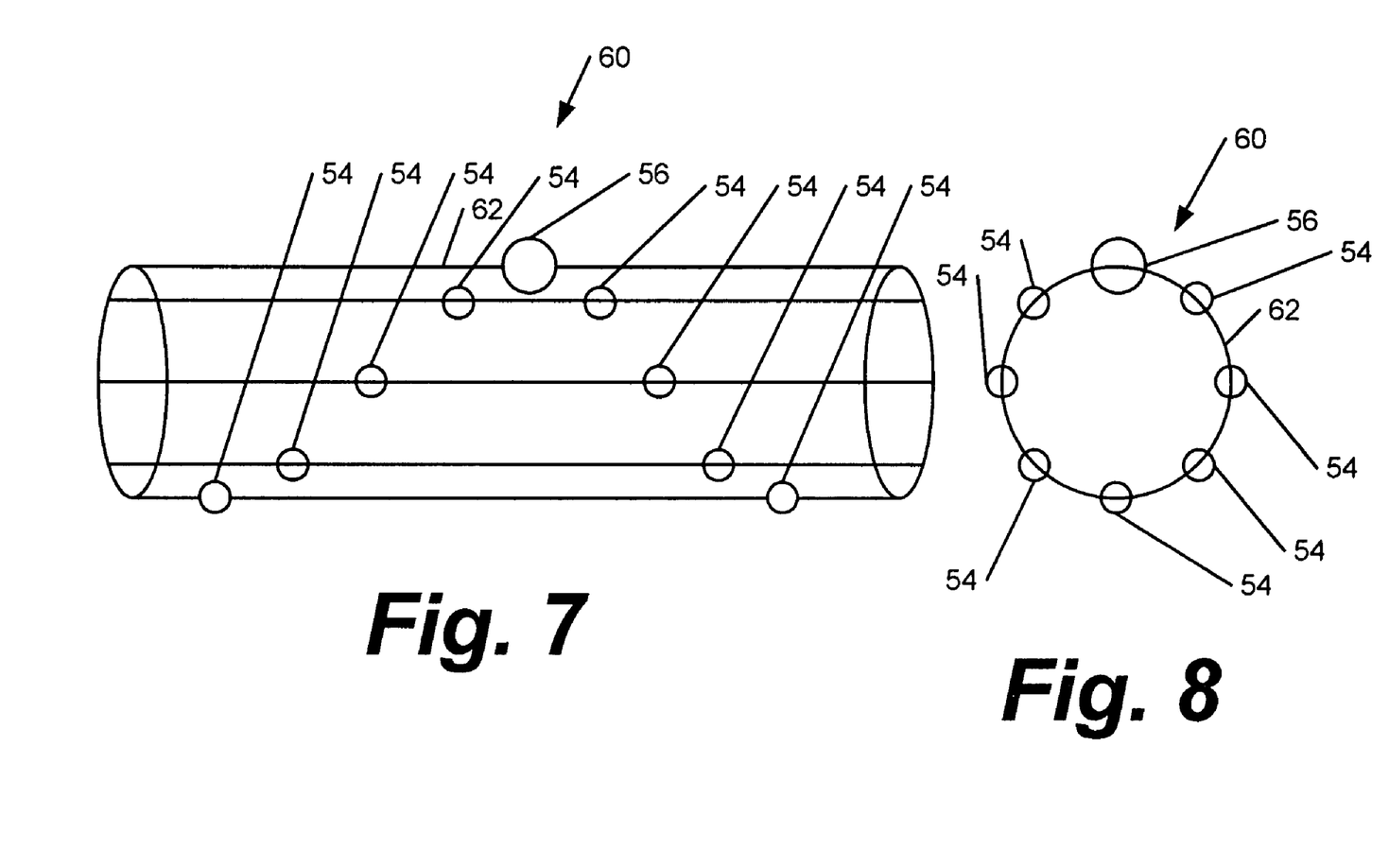
FIG. 7 is a longitudinal side view of a configuration of a phantom of the present invention having a transparent or essentially transparent supporting structure comprising a wire frame.
FIG. 8 is an end view of the phantom configuration of FIG. 7.
Figure 9:
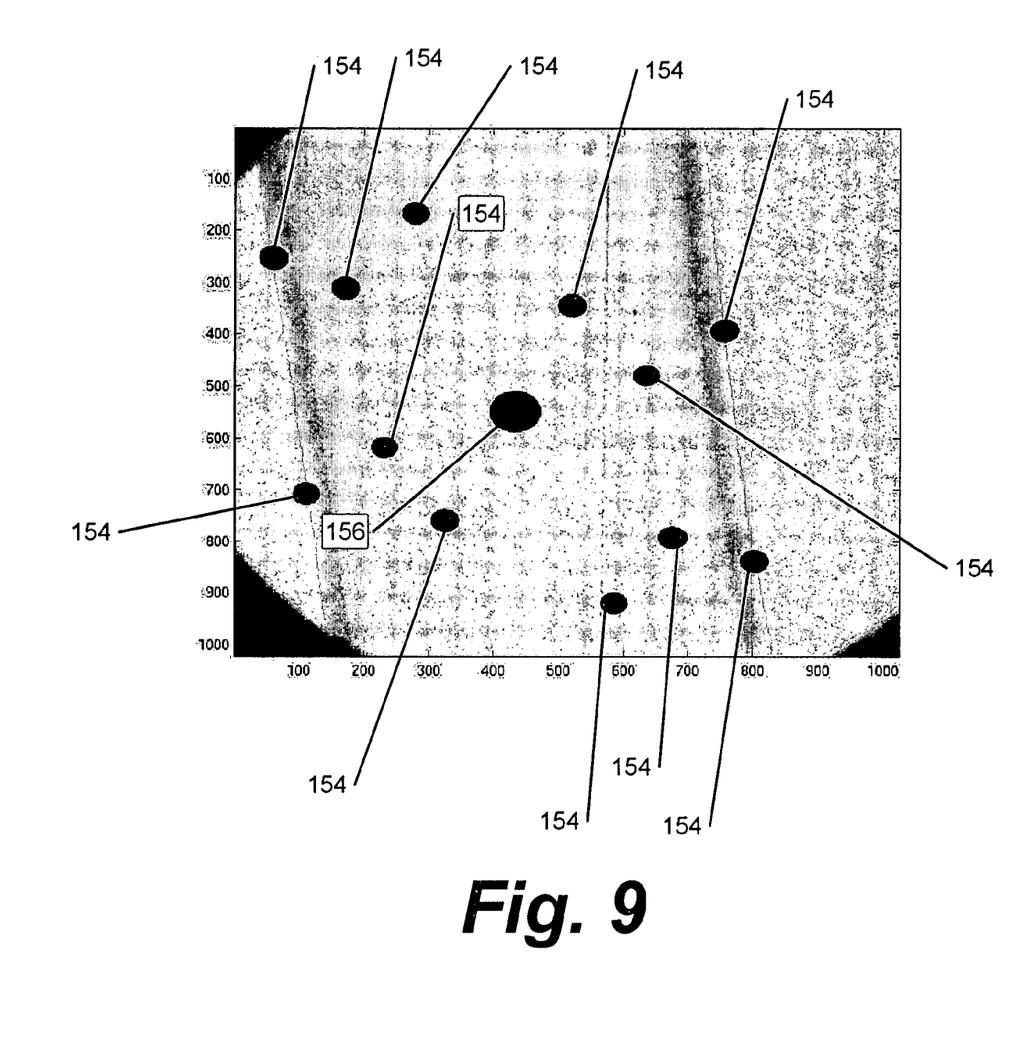
FIG. 9 is an example of an image resulting from a scan of a phantom configuration of the present invention exemplified by FIGS. 5 and 6 using the CT imaging apparatus configuration of FIGS. 1 and 2.

Referring again to FIG. 1 and FIG. 2, a scanning volumetric computed tomography system 10 has a rotation axis, a rotation plane (not explicitly shown in FIG. 1 or FIG. 2, but essentially represented by the plane of the paper in the representation of imaging system 10 in FIG. 2), an x-ray source 14, and a detector 18. To determine the geometry of system 10, a phantom having a series of discrete markers 54 and 56 spatially separated along the rotational axis of tomography system 10 is scanned (instead of patient 22, as shown in FIG. 1 and FIG. 2). Various phantom configurations can be used, such as phantom 50 of FIG. 3 and FIG. 4, phantom 58 of FIG. 5 and FIG. 6, or phantom 60 of FIG. 7 and FIG. 8 can be used. In each of these phantoms, markers 54 and 56 are configured on a supporting structure so as to permit separate identification of each marker within the collection of projection images. An example of a projection image generated with a volumetric computed tomography system is shown in FIG. 9; the phantom has discrete opaque markers 54 and 56 embedded on the surface of a plastic cylinder in a helical pattern as shown in FIG. 7 and FIG. 8. Images of markers 54 are denoted 154, whereas the image of marker 56 is denoted 156. Individual markers 54 represented by each image 154 can be uniquely identified from the relationship of their images 154 with one another and with image 156 of marker 56. Images 154 and 156 of markers 54 and 56 are located in each projection image, and the located positions of each marker within the collection of projection images are assigned to tracks. Using the assigned tracks, a relative alignment between the detector, the source, and the rotation axis of CT system 10 is determined.

Figure 10:
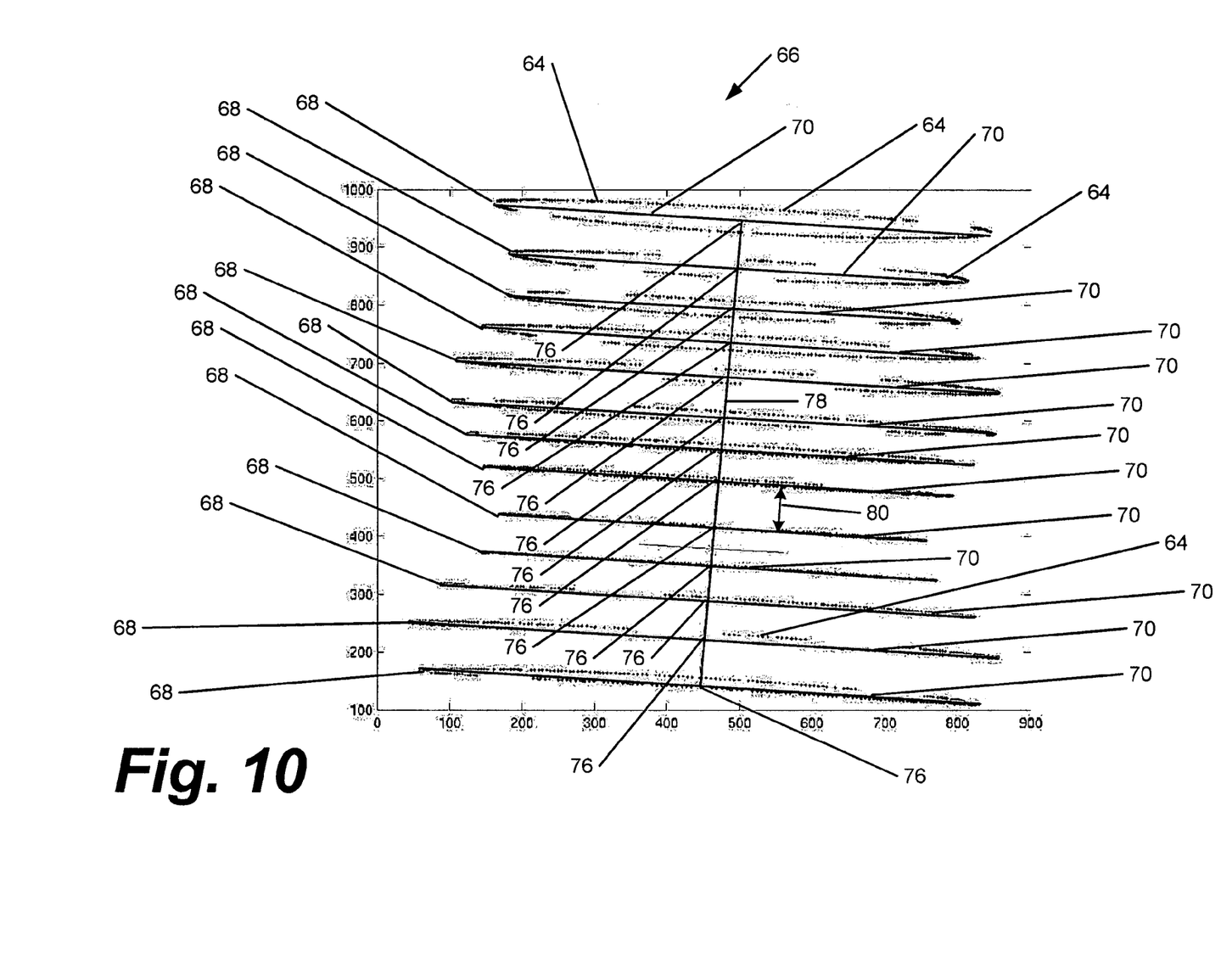
FIG. 10 is an example of a plot obtained by scanning a phantom configuration of the present invention that can be used to determine the geometry of the CT imaging apparatus configuration of FIGS. 1 and 2.

More particularly, because of the geometry of CT system 10, each marker 54 or 56 traces out an elliptical trajectory on detector 18 as rotation of the phantom about the axis of rotation in the volumetric CT system occurs. Markers 54 and 56 are uniquely identified from their locations relative to marker 56, and the center of each marker 54 and 56 is determined from the image of each marker 154 and 156 in FIG. 9 respectively. Referring to FIG. 10, these centers 64 are superimposed on a single plot 66. (FIG. 10 is not intended to represent the same scan or the same phantom that produced the data shown in FIG. 9. Plot 66 is, however, from an experiment in which data was corrupted in some views. Therefore, gaps in plot 66 represent regions in which images 154 and 156 of particular markers 54 and 56, respectively, were missing. In plot 66, centers 64 of markers 54 and 56, as determined from images 154 and 156, respectively, are shown, therefore there is no distinction in plot 66 between markers 54 and marker 56. Because of the large number of centers 64, only a few are indicated by call outs in FIG. 10.) Plot 66 is a set of detector coordinates occupied by the center 64 of each marker 54 and 56 at some time during a scan. (Centers 64 actually represent the locations of centers of images 154 and 156 of markers 54 and 56, respectively; however, to facilitate description of the invention, these centers 64 will simply be denoted as the centers of markers 54 and 56.) Each elliptical track 68 is fit to a line segment 70 using, for example, by an orthogonal regression. Line segments 70 fit a major axis of an ellipse for each track 68. Line segments 70 are bisected to determine geometric centers of the elliptical trajectories of the center 64 of markers 54 and 56 on detector 18. A bisector 76 is determined for each line segment 70 corresponding to each track 68. A line 78 is then fitted to bisectors 76. Line 78 represents the projection of the rotation axis z of imaging system 10 on the detector. Line 78 can be used as a calibration measurement to adjust the relative alignment between detector 18 and rotation axis z 78.

The minor axis of the trajectory of centers 64 of markers 54 and 56 in the plane of rotation is zero, i.e., the trajectory forms a line on the detector. Thus, for each marker 54 and 56, the residual error between the linear fit of trajectory 68 and the marker positions 64 is determined. Using residual errors along with quadratic interpolation techniques for determining a minimum, the projection of the rotation plane onto detector 18 is identified. The projected axis of rotation and the projected plane of rotation are sufficient for either physical adjustment of the geometry of imaging system 10 or to determine a compensating reconstruction process to provide full image quality from data sets acquired with volumetric imaging system 10.

In some configurations, magnification of imaging system 10 is determined using line segments 70. Spacing 80 between two line segments 70 is equal to the magnification of imaging system 10 times the true spacing between the two centers 64 of markers 54 (or between 54 and 56, depending upon the line segments selected) represented by the corresponding line segments.

In various configurations of the present invention, a calibration phantom configuration (such as phantom 50, 58, or 60) is positioned so that not all of markers 54 and 56 are on the axis of rotation z of imaging system 10. As a result, elliptical trajectories 68 of marker centers 64 are more easily resolved.

Although an imaging system 10 having a gantry 12 is illustrated in FIG. 1 and FIG. 2, various configurations of the present invention are also useful for benchtop-type imaging devices. Although various configurations of the present invention are described in conjunction with medical CT imaging devices, the present invention imposes no requirement that the CT imaging device be designed or used for medical purposes. The present invention is equally useful in conjunction with CT imaging devices designed or used for non-medical purposes and is also not limited to computed tomographic systems employing x-rays. For example, the present invention is useful in any computed tomography configuration in which transmission measurements are obtained, such as optical imaging from a point source.

It will thus be appreciated that configurations of the present invention allow for a relatively simple determination of various geometric parameters of a volumetric computed tomographic system that is resistant to measurement errors and phantom construction errors. Configurations of the present invention are also useful with a wide range of geometries and magnifications, as well as imaging modalities.

While the invention has been described in terms of various specific embodiments, those skilled in the art will recognize that the invention can be practiced with modification within the spirit and scope of the claims.

What is claimed is:

1. A method for determining geometry of a scanning volumetric computed tomographic (CT) system, said system having a rotation axis, a rotation plane, an x-ray source, and a detector, said method comprising:
    scanning a phantom having a series of spatially separated discrete markers with the scanning volumetric computed tomographic system, said markers configured on a supporting structure of the phantom so as to permit separate identification of each said marker in a collection of projection images;
    locating images of the markers in each projection image;
    using the located marker images to assign marker locations to tracks; and
    using the assigned tracks for determining a relative alignment between the detector, the source, and the rotation axis of the scanning volumetric computed tomographic system.

2. A method in accordance with claim 1 wherein said determining a relative alignment between the detector, the source, and the rotation axis comprises utilizing orthogonal regression to fit each track to a line segment, and fitting a line through bisecting points of the line segments to determine a projection of the rotation axis of the scanner onto the detector.

3. A method in accordance with claim 2 further comprising determining residual errors between said line segments and said tracks, and utilizing said residual errors to determine a projection of the rotation plane onto the detector.

4. A method in accordance with claim 3 further comprising utilizing the determined projection of the rotation plane and the determined projection of the rotation axis to adjust a geometry of the scanning volumetric computed tomography system.

5. A method in accordance with claim 3 further comprising utilizing the determined projection of the rotation plane and the determined projection of the rotation axis to compensate an image reconstruction process of the scanning volumetric computed tomography system.

6. A method in accordance with claim 2 further comprising determining a magnification of the CT system utilizing a spacing between line segments fitted to the assigned tracks.

7. A method in accordance with claim 1 wherein the markers are metal spheres of equal size except for one metal sphere larger than the others.

8. A method in accordance with claim 1 further comprising adjusting a geometry of the scanning volumetric CT imaging system.

9. A method in accordance with claim 1 wherein the spatially separated discrete markers are spaced along a line parallel to the rotation axis of the volumetric CT imaging system.

10. A method in accordance with claim 1 wherein the spatially separated discrete markers are spaced along a helix.

11. A method in accordance with claim 1 further comprising orienting the phantom in the scanning volumetric CT imaging system so that trajectories of the scanned markers do not intersect one another.

12. A method in accordance with claim 1 wherein said using the located marker images to assign marker locations to tracks comprises using the located marker images to determine marker center locations, and assigning the determined marker center locations to tracks.

13. A method for determining geometry of a scanning volumetric computed tomographic (CT) system, said system having a rotation axis, a rotation plane, a radiation source other than an x-ray source, and a detector, said method comprising:
    scanning a phantom having a series of spatially separated discrete markers with the scanning volumetric computed tomographic system utilizing the radiation source other than an x-ray source, said markers configured on a supporting structure of the phantom so as to permit separate identification of each said marker in a collection of projection images;
    locating images of the markers in each projection image;
    using the located marker images to assign marker locations to tracks; and
    using the assigned tracks for determining a relative alignment between the detector, the source, and the rotation axis of the scanning volumetric computed tomographic system.

14. A method in accordance with claim 13 further comprising adjusting a geometry of the volumetric CT imaging system.

15. A method in accordance with claim 13 wherein the spatially separated discrete markers are spaced along a line parallel to the rotation axis of the volumetric CT imaging system.

16. A method in accordance with claim 13 wherein the spatially separated discrete markers are spaced along a helix.

17. A method in accordance with claim 13 further comprising orienting the phantom in the volumetric CT imaging system so that trajectories of the scanned markers do not intersect one another.

18. A method in accordance with claim 13 wherein said using the located marker images to assign marker locations to tracks comprises using the located marker images to determine marker center locations, and assigning the determined marker center locations to tracks.

* * * * *